(12) United States Patent
Luo et al.

(10) Patent No.: US 11,014,886 B2
(45) Date of Patent: May 25, 2021

(54) METHOD FOR PREPARING 2,2'-DIPYRIDINE AND DERIVATIVES THEREOF

(71) Applicant: NANJING REDSUN BIOCHEMISTRY CO., LTD., Jiangsu (CN)

(72) Inventors: Chaoran Luo, Jiangsu (CN); Wenkui Wang, Jiangsu (CN); Yi Xue, Jiangsu (CN); Xinchun Chen, Jiangsu (CN); Dianhai Zhou, Jiangsu (CN); Jianhua Jiang, Jiangsu (CN); Fujun Wang, Jiangsu (CN)

(73) Assignee: NANJING REDSUN BIOCHEMISTRY CO., LTD., Jiangsu (CN)

( * ) Notice: Subject to any disclaimer, the term of this patent is extended or adjusted under 35 U.S.C. 154(b) by 0 days.

(21) Appl. No.: 16/764,538

(22) PCT Filed: Apr. 4, 2018

(86) PCT No.: PCT/CN2018/081950
§ 371 (c)(1),
(2) Date: May 15, 2020

(87) PCT Pub. No.: WO2019/095613
PCT Pub. Date: May 23, 2019

(65) Prior Publication Data
US 2020/0331857 A1    Oct. 22, 2020

(30) Foreign Application Priority Data
Nov. 17, 2017   (CN) .......................... 201711144623.6

(51) Int. Cl.
*C07D 213/22* (2006.01)
*B01J 21/14* (2006.01)
*B01J 23/889* (2006.01)
*B01J 35/10* (2006.01)

(52) U.S. Cl.
CPC ............ *C07D 213/22* (2013.01); *B01J 21/14* (2013.01); *B01J 23/8892* (2013.01); *B01J 35/1019* (2013.01); *B01J 35/1042* (2013.01); *B01J 35/1047* (2013.01); *B01J 35/1061* (2013.01)

(58) Field of Classification Search
CPC ............. C07D 213/22; C07D 213/127; C07D 213/61; B01J 21/14; B01J 35/1019; B01J 35/1047; B01J 35/1042; B01J 35/1061; B01J 23/8892; B01J 2523/00; B01J 21/12; B01J 23/755; B01J 37/0201; B01J 37/0207; B01J 37/0213; B01J 21/10; B01J 23/002; B01J 23/83
USPC ........................................................ 546/260
See application file for complete search history.

(56) References Cited

FOREIGN PATENT DOCUMENTS

| CN | 101219988 | | 7/2008 |
|---|---|---|---|
| CN | 105859610 | | 8/2016 |
| CN | 106380444 | | 2/2017 |
| CN | 106699642 | * | 5/2017 |
| WO | WO9201674 | | 2/1992 |

* cited by examiner

*Primary Examiner* — Taylor V Oh
(74) *Attorney, Agent, or Firm* — Gary J. Gershik

(57) ABSTRACT

Disclosed is a method for preparing 2,2'-dipyridine and derivatives thereof. The method includes: using pyridine represented by formula I or a derivative thereof as a raw material to generate 2,2'-dipyridine represented by formula II by performing dehydrogenative coupling under the action of a supported catalyst in the presence of additives, where R is H, $C_1$-$C_2$ alkyl, Cl, or Br. The method of the present invention features wide adaptability to raw materials, high atomic utilization rate, high catalyst activity, long service life, and fewer by-products.

14 Claims, No Drawings

METHOD FOR PREPARING 2,2'-DIPYRIDINE AND DERIVATIVES THEREOF

RELATED APPLICATIONS

This application is a § 371 national stage of PCT International Application No. PCT/CN2018/081950, filed Apr. 4, 2018, and claims priority of Chinese Application No. 201711144623.6, filed Nov. 17, 2017, the contents of each of which are hereby incorporated by reference into this application.

BACKGROUND

Technical Field

The present invention belongs to the field of fine chemical engineering and organic synthesis, and particularly relates to a method for preparing 2,2'-dipyridine and derivatives thereof.

Related Art

There are many methods for preparing 2,2'-dipyridine, for example, a method of firstly preparing a pyridine-N-oxide from a compound containing pyridine groups, performing catalytic coupling by a metal catalyst and then performing deoxygenation to obtain 2,2'-dipyridine (Application No.: 201510291441.6, U.S. Pat. No. 3,290,321); a method for coupling by using a pyridine Grignard reagent (Application No.: 201410452176.9); a Ullmann method for coupling by using halogenated pyridine as a raw material (M. Tiecco, etc., Communications, 1984, 736-738); a method for directly coupling pyridine or a pyridine derivative through a metal catalyst (U.S. Pat. No. 5,416,217, GB1014076), etc.

Parts of the above methods can reach a high conversion rate, but all methods have some defects, which limit their industrialization prospects. The method for preparing 2,2'-dipyridine through coupling by using a pyridine-N-oxide as a raw material needs deoxygenation after coupling. Chinese patent ZL201510291441.6 uses phosphorus trichloride as a deoxygenation reagent, a molar ratio of the phosphorus trichloride to the raw material is 1:1 to 1.2, and consumption of the phosphorus trichloride is high, so that much phosphorus-containing wastewater is generated in a process, and is difficult to treat. The most important step in the method for preparing 2,2'-dipyridine through coupling by using the Grignard reagent is to prepare the Grignard reagent, this step has strict requirements on the moisture content, and the Grignard reagent is unstable and is difficult to realize mass production. The Ullmann method realizes industrialization, and was one of mainstream methods for preparing 2,2'-dipyridine several years ago, but this method uses triphenylphosphine and metal salts as catalysts, and also needs metal as a reducing agent, so that a great amount of solid waste is generated, and is difficult to treat. Additionally, this method uses 2-halogenated pyridine as a raw material, and an atomic utilization rate of the raw material is not high, so that this method has gradually become obsolete in recent years. A method of direct dehydrogenative coupling of pyridine or a pyridine derivative through a metal catalyst is a promising method. The study of this method was concentrated in the 1950s. Normal pressure and 115° C. were mainly used for preparation, but the catalyst activity was low, and can only reach 0.06 g 2,2'-dipyridine/g catalyst/h, and the service life was short, and can only reach less than 100 h. At the end of the 20th century, U.S. Pat. No. 5,416,217 disclosed a method for preparing 2,2'-dipyridine by using a supported nickel catalyst at 0.9 MPa and 180 to 215° C., the catalyst activity reached up to 0.1 g/g/h and the service life was greater than 500 h. In the process of preparing 2,2'-dipyridine by the inventor by this method, a great number of by-products of 2-methylpyridine were generated, of which the reason maybe that pyridine underwent pyrolysis with the supported nickel catalyst at high temperature and high pressure, methyl radicals were generated, and 2-methylpyridine more easily generated in reaction kinetics was generated. Additionally, this method is only applicable to pyridine, 2-methylpyridine, and 4-methylpyridine.

SUMMARY

The objective of the present invention is to overcome the defects in the prior art and provide a method for preparing 2,2'-dipyridine and derivatives thereof which features high atomic utilization rate, high catalyst activity, long service life, few by-products, and wide adaptability to raw materials.

The objective of the present invention is achieved through the following technical solution:

A method for preparing 2,2'-dipyridine and derivatives thereof uses pyridine represented by formula I or a derivative thereof as a raw material to generate 2,2'-dipyridine represented by formula II by performing dehydrogenative coupling under the action of a supported catalyst in the presence of additives.

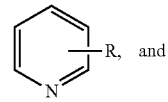

Formula I

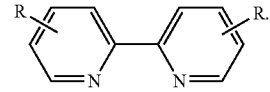

formula II

R is H, $C_1$-$C_2$ alkyl, Cl, or Br. In formula I, R is an α, β or γ-substituent group of pyridine.

2,2'-dipyridine represented by formula II is specifically as follows:

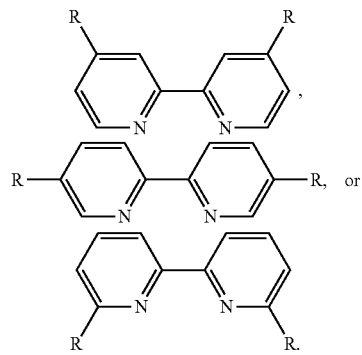

Specifically, pyridine or the derivative thereof is selected from 2-methylpyridine, 3-methylpyridine, 4-methylpyridine, 2-ethylpyridine, 3-ethylpyridine, 4-ethylpyridine, 2-chloropyridine, 3-chloropyridine, 2-bromopyridine, 3-bromopyridine, etc.

A support of the supported catalyst is a composite support composed of γ-$Al_2O_3$, $SiO_2$, and MgO. A content of $SiO_2$ is 2 to 5%. A content of MgO is 2 to 5%. The balance is γ-$Al_2O_3$.γ-$Al_2O_3$ is used as a main component of the support. The objective of $SiO_2$ is to improve a specific surface area of a γ-$Al_2O_3$ support, but pyrolysis of pyridine will be promoted by acidity of $SiO_2$ to increase a generation amount of by-products of 2-methylpyridine, so MgO is introduced as a basic component to reduce the acidity of the support. Additionally, through formation of magnesium aluminate spinel, stability of a support structure can be improved.

A specific surface area of the $Al_2O_3$—$SiO_2$—MgO composite support should be greater than 120 $m^2$/g, and is preferably 150 to 300 $m^2$/g. A pore volume should be greater than 0.5 mL/g, and is preferably 0.5 to 1.5 $m^2$/g. Molecules of the 2,2'-dipyridine are great, so that a pore diameter of a used support is at least greater than a molecule diameter of the 2,2'-dipyridine. The pore diameter should ≥10 nm. The pore diameter being ≥10 nm accounts for 60% of the pore volume. On the basis, the pore diameter should be distributed in a narrow range, and is preferably 10 to 20 nm, and the pore diameter of 10 to 20 nm accounts for at least 30% of the pore volume, preferably 30 to 95%. The composite support is in a spherical shape, a cylindrical shape, or a clover shape, preferably in the spherical shape and the clover shape.

A supported metal of the supported catalyst is a mixture of any two or more of nickel and manganese, lanthanum, or cerium. A main component is nickel. A supported amount of nickel does not exceed 20%, and is preferably 5 to 20%. A supported amount of manganese does not exceed 0.5%. A supported amount of lanthanum does not exceed 0.5%. A supported amount of cerium does not exceed 0.5%. The effect of manganese, lanthanum, and cerium is to enable nickel crystalline grains to be more dispersed on a surface of the catalyst, inhibit the increase speed of the nickel crystalline grains in a catalytic reaction process, and promote the structural stability of the catalyst.

The $Al_2O_3$—$SiO_2$—MgO composite support of the present invention is prepared by a method known in the art. The supported catalyst of the present invention is prepared from the composite support by an impregnation method. The impregnation method is specifically as follows: the composite support is impregnated into a nickel nitrate ($Ni(N_3)_2$) water solution for 24 h, filtration is performed, drying is performed for 5 h under the conditions of 120° C. and 50 kpa, and then, roasting is performed for 5 h at 400° C. to obtain a primarily impregnated catalyst solid. The obtained catalyst solid is impregnated into a mixed water solution prepared from $Ni(NO_3)_2$ and at least two metal salts selected from $Ce(NO_3)_3$, $La(NO_3)_3$, and $Mn(NO_3)_2$ for 24 h, filtration is performed, drying is performed for 5 h under the conditions of 120° C. and 50 kpa, and then, roasting is performed for 5 h at 400° C. to obtain a secondarily impregnated catalyst solid. The secondarily impregnated catalyst solid is subjected to reduction treatment to reduce metal oxides into metal elements to obtain the supported catalyst. The secondarily impregnated catalyst solid is filled into a reaction device, and mixed gas of nitrogen gas and hydrogen gas is introduced from an upper part at a gas speed of 10 L/h. A content of the nitrogen gas (volume percentage) is 99%. A content of the hydrogen gas is 1%. A temperature rise speed is controlled to be 1° C./min to raise the temperature to 450° C. Heat insulation is performed for 2 h at 450° C. At the same time, the content of the hydrogen gas is uniformly increased to 99% from 1%. The content of the nitrogen gas is uniformly reduced to 1% from 99%. Then, heat insulation is performed for 3 h. Heating is stopped. Gas introduction is stopped after the temperature is lowered to the room temperature, and the supported catalyst of the present invention is obtained.

The additives are $C_1$-$C_5$ straight chain alcohol or $C_1$-$C_5$ ester compounds. The $C_1$-$C_5$ straight chain alcohol compounds are methyl alcohol, ethyl alcohol, propyl alcohol, butyl alcohol, or amyl alcohol. The $C_1$-$C_5$ ester compounds are methyl formate, methyl acetate, and ethyl acetate. Consumption of the additives is 0.05 to 0.3% wt of pyridine or the derivative thereof.

The method for preparing 2,2'-dipyridine and derivatives thereof of the present invention includes: pyridine or a derivative thereof and additives enter a reaction device from the bottom of a fixed bed reaction device, a dehydrogenative coupling reaction is performed under the action of a supported catalyst, reaction liquid flows out from the top of the reaction device to enter a gas-liquid separator, and a material is discharged from the gas-liquid separator. If the raw material is pyridine, a light-component mixture and a 2,2'-dipyridine crude product are separated from the material discharged from the gas-liquid separator through distillation at 115 to 130° C. and a normal pressure, and pyridine and by-products of 2-methylpyridine are separated from the light-component mixture through rectification. If the raw material is the pyridine derivative, a light-component mixture and a 2,2'-dipyridine crude product are separated from the material discharged from the gas-liquid separator through distillation at 115 to 130° C. and 20 to 30 kpa. The 2,2'-dipyridine crude product or the 2,2'-dipyridine derivative crude product with a boiling point lower than 300° C. at a normal pressure is purified through rectification. A solvent such as methyl alcohol and petroleum ether with the same weight as the crude product is added into the 2,2'-dipyridine derivative crude product with a boiling point higher than 300° C. at a normal pressure for recrystallization purification.

The temperature of the coupling reaction is 150 to 400° C., preferably 180 to 300° C., and the pressure of the coupling reaction is 0.55 to 2.4 Mpa.

The total feeding flow rate of the raw material and the additives is 0.025 to 0.3 mL/g catalyst/min, preferably 0.028 to 0.3 mL/g catalyst/min.

The fixed bed reaction device is a fixed bed tube reactor.

DETAILED DESCRIPTION

Embodiment 1: Preparation of Catalyst Support

A catalyst support was prepared by a pH swing method. The method was from articles of T. Ono, etc. (T. Ono, et., Studies in Surface Science and Catalysis, Vol. 16, 1983, 631-641).

A solution I was prepared: 1125 g of $Al(NO_3)_3$ 9.$H_2O$ was taken and dissolved into 1705 g of distilled water, and pH=2.2.

A solution II was prepared: 70 g of NaOH was taken and dissolved into 118 g of distilled water to prepare an NaOH water solution. 85 g of $Al(OH)_3$ was added to prepare an $NaAlO_2$ solution through stirring for more than 1 h. The solution was heated to 90° C. and stirred for more than 2 h. Then, a proper amount of distilled water was added to reach a total mass of the solution of 278 g, and the solution pH=10.

The solution I and the solution II were respectively poured into two funnels, and the funnels were connected onto a four-neck flask with stirring. 700 g of distilled water was contained in the four-neck flask, and was heated to 75° C. by ethylene glycol. The solution I was dripped into the four-neck flask. When the pH in the four-neck flask=3, the solution II was slowly dripped (the dripping time exceeded 5 min). When the pH in the four-neck flask=9, dripping of the solution II was stopped. After stirring for 5 min, a second round of dripping of the solution I was started, so that the pH=3. Then, the solution II was dripped, so that the pH=9.4 rounds were repeated in such a way. Before a 5th round was started, a certain amount of $Mg(NO_3)_2 \cdot 6H_2O$ was added into the solution I, a certain amount of $Na_4SiO_4$ was added into the solution II, and other steps were identical to those in the previous 4 rounds. After being filtered, obtained alumina hydrogel was washed by distilled water until a content of Na in filtrate was 0.03% lower than a content of Al in filter cake. The filter cake was made into clover-shaped extruded rubber with length of 2.5 to mm and a diameter of 0 to 1.5 mm, and the extruded rubber was put into a drying oven to be dried for more than 4 h at 120° C., and was roasted for more than 3 h in a muffle furnace at 500° C. to prepare the $Al_2O_3$—$SiO_2$—MgO composite support.

Amounts of added $Mg(NO_3)_2 \cdot 6H_2O$ and $Na_4SiO_4$ are as shown in Table 1.

TABLE 1

Content of Magnesium Oxide and Silicon Dioxide in Support

| Support number | Consumption of magnesium nitrate hexahydrate (g) | Content of magnesium oxide (%) | Content of sodium silicate (g) | Content of silicon dioxide (%) |
|---|---|---|---|---|
| a | 1.03 | 2 | 0.49 | 2 |
| b | 2.72 | 5 | 1.04 | 4 |
| c | 1.58 | 3 | 0.76 | 3 |
| d | 1.60 | 3 | 1.02 | 4 |
| e | 1.07 | 2 | 1.27 | 5 |

Characterization parameters of the prepared support are as shown in Table 2:

TABLE 2

Characterization of Support

| Support number | Specific surface area (m²/g) | Pore volume (mL/g) | Pore diameter distributed in pore volume | | |
|---|---|---|---|---|---|
| | | | 2 nm ≤ pore diameter < 10 nm | 10 nm ≤ pore diameter ≤ 20 nm | 20 nm < pore diameter ≤ 100 nm |
| a | 221 | 0.68 | 0.12 | 0.22 | 0.23 |
| b | 272 | 1.12 | 0.09 | 0.62 | 0.32 |
| c | 253 | 0.98 | 0.15 | 0.71 | 0.11 |
| d | 268 | 1.09 | 0.21 | 0.54 | 0.15 |
| e | 291 | 1.32 | 0.12 | 0.94 | 0.09 |

Embodiment 2: Preparation of Supported Catalyst

A support was selected and used as a catalyst support. A proper amount of $Ni(NO_3)_2 \cdot 6H_2O$ was weighed to be prepared into 150 g of a water solution with a certain concentration with water. 100 g of the support was impregnated in the water solution for 24 h, filtered, put into a drying box to be dried for 5 h under the conditions of 120° C. and 50 kpa. An obtained dry solid was roasted for 5 h at 400° C. to obtain a primarily impregnated catalyst solid. The catalyst solid was impregnated for 24 h in 100 g of a water solution of a mixture of $Ni(NO_3)_2$, $Ce(NO_3)_3$, $La(NO_3)_3$, and $Mn(NO_3)_2$ with a certain concentration, the subsequent drying and roasting conditions were identical to those of the first time, and a secondarily impregnated catalyst solid was obtained. The addition amount of supported metal salts is as shown in Table 3.

The secondarily impregnated catalyst solid was reduced: the prepared secondarily impregnated catalyst solid was taken and was charged into a stainless steel pipe with an inner diameter of 19 mm and a length of 600 mm, and a design pressure of the stainless steel pipe was 2.5 Mpa. Mixed gas of nitrogen gas and hydrogen gas was introduced from an upper part of the stainless steel pipe at a gas speed of 10 L/h. A content of the nitrogen gas was 99%, and a content of the hydrogen gas was 1%. The stainless steel pipe was covered with an electric heating jacket for heating. A temperature was raised to 450° C. from the room temperature at a speed of 1° C./min, and heat insulation was performed for 5 h at 450° C. Within first 2 h of heat insulation, the content of the hydrogen gas was uniformly increased to 99% from 1%, and the content of the nitrogen gas was uniformly reduced to 1% from 99%. After heat insulation for 5 h, heating was stopped. Gas introduction was stopped after a temperature of a catalyst bed layer was reduced to the room temperature, and the supported catalyst was obtained.

TABLE 3

Addition Amount of Supported Metal Salts of Catalyst and Supported Amount of Metal in Supported Catalyst

| Catalyst number | Primary impregnation Addition amount of nickel salt* (g) | Secondary impregnation Addition amount of nickel salt (g) | Addition amount of cerium salt* (g) | Addition amount of manganese salt* (g) | Addition amount of lanthanum salt* (g) | Supported amount of nickel (%) | Supported amount of cerium (%) | Supported amount of manganese (%) | Supported amount of lanthanum (%) |
|---|---|---|---|---|---|---|---|---|---|
| A | 5.18  | 2.22 | 0.093 | 0.783 | 0.093 | 5  | 0.1 | 0.5 | 0.1 |
| B | 10.36 | 4.44 | —     | 0.626 | 0.467 | 10 | —   | 0.4 | 0.5 |
| C | 10.36 | 4.44 | 0.093 | 0.626 | —     | 10 | 0.1 | 0.4 | —   |
| D | 10.36 | 4.44 | 0.186 | 0.783 | 0.187 | 10 | 0.2 | 0.5 | 0.2 |
| E | 10.36 | 4.44 | 0.093 | 0.470 | 0.187 | 10 | 0.1 | 0.3 | 0.2 |
| F | 15.54 | 6.66 | —     | 0.313 | 0.280 | 15 | —   | 0.2 | 0.3 |
| G | 15.54 | 6.66 | 0.186 | 0.157 | —     | 15 | 0.2 | 0.1 | —   |
| H | 15.54 | 6.66 | 0.279 | 0.470 | 0.187 | 15 | 0.3 | 0.3 | 0.2 |
| I | 20.72 | 8.88 | —     | 0.783 | 0.093 | 20 | —   | 0.5 | 0.1 |
| J | 20.72 | 8.88 | 0.186 | 0.783 | —     | 20 | 0.2 | 0.5 | —   |
| K | 20.72 | 8.88 | 0.093 | —     | 0.187 | 20 | 0.1 | —   | 0.2 |
| L | 20.72 | 8.88 | 0.186 | 0.470 | 0.093 | 20 | 0.2 | 0.3 | 0.1 |
| M | 20.72 | 8.88 | 0.465 | 0.157 | 0.374 | 20 | 0.5 | 0.1 | 0.4 |
| N | 20.72 | 8.88 | 0.372 | 0.626 | 0.374 | 20 | 0.4 | 0.4 | 0.4 |
| O | 20.72 | 8.88 | 0.093 | 0.626 | 0.093 | 20 | 0.1 | 0.4 | 0.1 |

*Note:

the nickel salt is $Ni(NO_3)_2 \cdot 6H_2O$.

The cerium salt is $Ce(NO_3)_3 \cdot 6H_2O$.

The manganese salt is $Mn(NO_3)_2 \cdot 6H_2O$.

The lanthanum salt is $La(NO_3)_3 \cdot 6H_2O$.

Embodiment 3

35 g of the supported catalyst prepared in Embodiment 2 was taken, and charged into a stainless steel pipe with an inner diameter of 19 mm and a length of 600 mm, and a design pressure of the stainless steel pipe was 2.5 Mpa.

With reference to parameters in Table 4, the stainless steel pipe was heated to raise the temperature to a reaction temperature. Pyridine or a pyridine derivative containing additives was pumped into the stainless steel pipe by a pump from the bottom of the stainless steel pipe at a certain flow rate. Reaction liquid flowed out from the top of the stainless steel pipe, and entered a 500 mL stainless steel gas-liquid separator to be received. The gas-liquid separator was provided with a back pressure valve and a pressure gauge. A cooling water jacket was disposed at the outside. Connection between the gas-liquid separator and a reactor were cut at intervals, a material in the gas-liquid separator was discharged, the pressure in the gas-liquid separator was supplemented to be identical to the pressure in the reactor, and then, the connection between the gas-liquid separator and the reactor was recovered for continuous reaction.

For a reaction system using pyridine as a raw material, a light-component mixture and a 2,2'-dipyridine crude product were separated from discharged reaction liquid through distillation at 115 to 130° C. and a normal pressure, and pyridine and by-products of 2-methylpyridine were separated from the light-component mixture through rectification. The plate number of a rectification tower was 68.4. A tower kettle temperature was 135° C. A tower top temperature was 115° C. Are flux ratio was 2.7:1. The separated pyridine was reused.

For a reaction system using the pyridine derivative as a raw material, a light-component mixture and a 2,2'-dipyridine derivative crude product were separated from discharged reaction liquid through distillation at 115 to 130° C. and 20 to 30 kpa, and the pyridine derivative was reused.

The 2,2'-dipyridine crude product and the 2,2'-dipyridine derivative crude product with a boiling point lower than 300° C. at a normal pressure were purified through rectification. A plate number of a rectification tower was 28.1. A pressure was 2.4 kpa. A tower kettle temperature was 190° C. A tower top temperature was 148° C. A reflux ratio was 0.3:1.

The 2,2'-dipyridine derivative crude product with a boiling point higher than 300° C. at a normal pressure was recrystallized and purified by a solvent such as methyl alcohol and petroleum ether, that is, the crude product was dissolved into the solvent with the same weight, the temperature was raised to 40° C., after dissolution, the temperature was reduced to 5° C. for crystallization, a solid was filtered out, drying was performed, a 2,2'-dipyridine derivative finished product was obtained, and crystallization mother liquid was reused.

Reaction results are as shown in Table 4:

TABLE 4

Catalyst Reaction Evaluation

| Catalyst number | Raw material | Additive | Consumption of additive (% wt) | Liquid phase flow rate (mL/min) | Reaction temperature (° C.) | Reaction pressure (Mpa) | Product (g/g catalyst) 2,2'-dipyridine | By-product* | Service life of catalyst (h) |
|---|---|---|---|---|---|---|---|---|---|
| A | Pyridine | Methyl alcohol | 0.05 | 1 | 180 | 0.55 | 825 | 28 | 1031 |
| B | Pyridine | Methyl alcohol | 0.15 | 2 | 180 | 0.55 | 1216 | 41 | 1501 |
| C | Pyridine | Ethyl alcohol | 0.3 | 5 | 180 | 0.55 | 1609 | 54 | 1962 |
| D | Pyridine | Ethyl alcohol | 0.2 | 8 | 180 | 0.55 | 2013 | 67 | 2548 |
| E | Pyridine | N-propyl alcohol | 0.05 | 10 | 180 | 0.55 | 2506 | 84 | 3133 |
| F | Pyridine | N-butyl alcohol | 0.15 | 10 | 200 | 0.75 | 2851 | 95 | 3564 |
| G | Pyridine | Ethyl acetate | 0.15 | 10 | 200 | 0.75 | 2643 | 88 | 3388 |
| H | Pyridine | Methyl acetate | 0.15 | 8 | 200 | 0.75 | 2412 | 80 | 3015 |
| I | Pyridine | Methyl formate | 0.15 | 8 | 200 | 0.75 | 2496 | 83 | 3120 |
| J | Pyridine | Methyl alcohol | 0.2 | 4 | 200 | 0.75 | 1523 | 51 | 1857 |
| K | Pyridine | Methyl alcohol | 0.2 | 4 | 220 | 1.05 | 1595 | 53 | 1994 |
| L | Pyridine | N-amyl alcohol | 0.2 | 6 | 220 | 1.05 | 1834 | 61 | 2293 |
| M | Pyridine | N-amyl alcohol | 0.2 | 6 | 220 | 1.05 | 1821 | 61 | 2248 |
| N | Pyridine | Ethyl acetate | 0.15 | 10 | 220 | 1.05 | 2744 | 91 | 3430 |
| O | Pyridine | Ethyl acetate | 0.15 | 10 | 220 | 1.05 | 2633 | 88 | 3291 |
| O | Pyridine | — | — | 10 | 220 | 1.05 | 30 | 6 | 268 |
| O | 4-methylpyridine | Ethyl acetate | 0.3 | 5 | 250 | 0.95 | 596 | — | 745 |
| O | 4-methylpyridine | — | — | 5 | 250 | 0.95 | 10 | — | 102 |
| O | 4-ethylpyridine | Ethyl acetate | 0.3 | 5 | 300 | 1.64 | 493 | — | 624 |
| O | 4-ethylpyridine | — | — | 5 | 300 | 1.64 | 2 | — | 63 |
| O | 2-ethylpyridine | Ethyl acetate | 0.3 | 5 | 300 | 2.26 | 565 | — | 706 |
| O | 2-ethylpyridine | — | — | 5 | 300 | 2.26 | 1 | — | 41 |
| O | 3-ethylpyridine | Ethyl acetate | 0.3 | 5 | 300 | 1.75 | 623 | — | 779 |
| O | 3-ethylpyridine | — | — | 5 | 300 | 1.75 | 1 | — | 47 |
| O | 2-chloropyridine | Methyl alcohol | 0.2 | 5 | 300 | 1.78 | 379 | — | 486 |
| O | 2-chloropyridine | — | — | 5 | 300 | 1.78 | 1 | — | 39 |
| O | 2-bromopyridine | Methyl alcohol | 0.2 | 5 | 300 | 2.19 | 385 | — | 481 |
| O | 2-bromopyridine | — | — | 5 | 300 | 2.19 | 0.8 | — | 29 |
| O | 3-chloropyridine | Ethyl alcohol | 0.2 | 5 | 300 | 2.38 | 412 | — | 515 |
| O | 3-chloropyridine | — | — | 5 | 300 | 2.38 | 0.5 | — | 28 |
| O | 3-bromopyridine | Ethyl alcohol | 0.2 | 5 | 300 | 1.78 | 423 | — | 529 |
| O | 3-bromopyridine | — | — | 5 | 300 | 1.78 | 0.6 | — | 21 |

Note:
by using pyridine as a raw material, a by-product is 2-methylpyridine.
By using 4-methylpyridine as a raw material, a product is 4,4'-dimethyl-2,2'-dipyridine.
By using 4-ethylpyridine as a raw material, a product is 4,4'-diethyl-2,2'-dipyridine.
By using 2-ethylpyridine as a raw material, a product is 6,6'-diethyl-2,2'-dipyridine.
By using 3-ethylpyridine as a raw material, a product is 5,5'-diethyl-2,2'-dipyridine.
By using 2-chloropyridine as a raw material, a product is 6,6'-dichloro-2,2'-dipyridine.
By using 2-bromopyridine as a raw material, a product is 6,6'-dibromo-2,2'-dipyridine.
By using 3-chloropyridine as a raw material, a product is 5,5'-dichloro-2,2'-dipyridine.
By using 3-bromopyridine as a raw material, a product is 5,5'-dibromo-2,2'-dipyridine.

g/g catalyst refers to a yield of 2,2'-dipyridine or a derivative thereof generated by per gram of catalyst in the service life period.

What is claimed is:
1. A method for preparing a compound of formula II comprising providing a compound of formula I and per- forming on the compound of formula I dehydrogenative coupling in the presence of a catalyst and an additive,

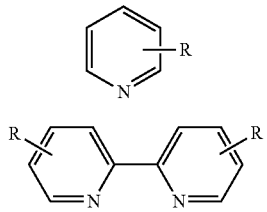

formula I formula II wherein R is H, $C_1$-$C_2$ alkyl, Cl, or Br;
wherein the catalyst is a mixture of nickel and a second metal selected from the group consisting of manganese, lanthanum and cerium; and
wherein the additive is a $C_1$-$C_5$ straight chain alcohol or a $C_1$-$C_5$ ester,
thereby preparing the compound of formula II.

2. The method for preparing a compound of formula II according to claim 1, wherein the catalyst is on a support, which support is an $Al_2O_3$—$SiO_2$—MgO composite.

3. The method for preparing a compound of formula II according to claim 2, wherein in the $Al_2O_3$—$SiO_2$—MgO composite support, a content of $SiO_2$ is 20 to 50, a content of MgO is 20 to 50, and the balance is $Al_2O_3$, by total weight of catalyst and support.

4. The method for preparing a compound of formula II according to claim 3, wherein an amount of nickel does not exceed 200, an amount of manganese if present does not exceed 0.50, an amount of lanthanum if present does not exceed 0.50, and an amount of cerium if present does not exceed 0.50, by total weight of catalyst and support.

5. The method for preparing a compound of formula II according to claim 3, wherein nickel is present at an amount of 5% to 20%.

6. The method for preparing a compound of formula II according to claim 2, wherein a specific surface area of the $Al_2O_3$—$SiO_2$—MgO composite support is greater than 120 $m^2$/g, a pore volume is greater than 0.5 mL/g, a pore diameter ≥10 nm, and the pore diameter being ≥10 nm accounts for 60% of the pore volume.

7. The method for preparing a compound of formula II according to claim 6, wherein the specific surface area of the $Al_2O_3$—$SiO_2$—MgO composite support is 150 to 300 $m^2$/g, the pore volume is 0.5 to 1.5 $m^2$/g, the pore diameter is 10 to 20 nm, and the pore diameter of 10 to 20 nm accounts for at least 300 of the pore volume.

8. The method for preparing a compound of formula II according to claim 1, wherein consumption of the additive is 0.05 to 0.3% wt of the compound of formula I.

9. The method for preparing a compound of formula II according to claim 1, wherein the $C_1$-$C_5$ straight chain alcohol is methyl alcohol, ethyl alcohol, propyl alcohol, butyl alcohol, or amyl alcohol, and the $C_1$-$C_5$ ester is methyl formate, methyl acetate, or ethyl acetate.

10. The method for preparing a compound of formula II according to claim 9, wherein consumption of the additive is 0.05 to 0.3% wt of the compound of formula I.

11. The method for preparing a compound of formula II according to claim 1, wherein a total liquid phase flow rate of the compound of formula I and the additive is 0.025 to 0.3 mL/g catalyst/min.

12. The method for preparing a compound of formula II according to claim 11, wherein the total liquid phase flow rate of the compound of formula I and the additive is 0.028 to 0.3 mL/g catalyst/min.

13. The method for preparing a compound of formula II according to claim 1, wherein the dehydrogenative coupling is performed at a temperature of 150° C. to 400° C., and at a pressure of 0.55 mPa to 2.4 mPa.

14. The method for preparing a compound of formula II according to claim 13, wherein the dehydrogenative coupling is performed at a temperature of 180° C. to 300° C.

* * * * *